United States Patent [19]

Kuchikata

[11] Patent Number: 5,092,918
[45] Date of Patent: Mar. 3, 1992

[54] GRANULES OF PYRIDINEDICARBOTHIOATE HERBICIDES

[75] Inventor: Masuo Kuchikata, Ibaraki, Japan

[73] Assignee: Monsanto Company, St. Louis, Mo.

[21] Appl. No.: 483,852

[22] Filed: Feb. 23, 1990

[51] Int. Cl.$^5$ .............................................. A01N 43/40
[52] U.S. Cl. .................... 71/94; 71/DIG. 1; 560/190
[58] Field of Search .............. 560/190; 71/94, DIG. 1

[56] References Cited

U.S. PATENT DOCUMENTS 3,944,662  3/1976  Miller, Jr. et al. .................... 424/78

OTHER PUBLICATIONS

Koho; "A Method for Controlling Digitaria in Turf by a Pyridinecarbothioate Derivative", vol. 112, 17759h, Chem. Abstract.

*Primary Examiner*—Marianne Cintins
*Assistant Examiner*—Jessica H. Nguyen
*Attorney, Agent, or Firm*—Stanley M. Tarter; Gordon F. Sieckmann; Howard C. Stanley

[57] ABSTRACT

The tendency of herbicidal pyridinedicarbothioates to crystallize and thus to partially lose herbicidal activity when formulated into granules is reduced by including in the granules a small, effective amount of a diester of an alkylene dicarboxylic acid.

6 Claims, No Drawings

GRANULES OF PYRIDINEDICARBOTHIOATE HERBICIDES

BACKGROUND OF THE INVENTION

1. Field of the Invention

The present invention relates to new and useful granules containing pyridinedicarbothioate herbicides. More particularly, the present invention relates to new and useful granules containing pyridinedicarbothioate herbicides wherein crystallization of the herbicides is reduced or suppressed over an extended period of time, such as during long term storage.

2. Prior Art

Herbicidal pyridinedicarboxylates are known in the patent literature. For example, Japanese published application (Kokai) 78,965 (1985) (U.S. Pat. No. 4,692,184) and 158,965 (1986) (U.S. Pat. No. 4,698,093) disclose certain pyridinedicarbothioate compounds as being effective in the control of undesirable weeds and other plants found in crops of transplanted rice. It has been found that when the known pyridinedicarbothioate compounds are formulated as solid formulations, such as extruded granules, dry flowable granules, etc., the compounds tend to crystallize and as a result have reduced herbicidal activity. Therefore, there is a need to provide granules having incorporated therein a herbicidally active pyridinedicarbothioate wherein the tendency of such active compound to crystallize is reduced or suppressed in order to minimize loss of herbicidal activity thereof.

SUMMARY OF THE INVENTION

In accordance with the present invention granules containing a herbicidal pyridinecarbcnioate having a reduced tendency to crystallize are provided by having incorporated therein a crystallizing inhibiting amount of a diester of an alkylene dicarboxylic acid. Crystallization of such herbicides adversely affects the activity thereof. Preferred esters for inhibiting the crystallization of the pyridinedicarboxylate herbicide in granular form are represented by the following formula

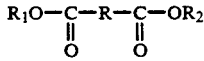

wherein R is an alkylene radical having from 1 to about 12 carbon atoms. $R_1$ and $R_2$ are independently alkyl radicals having from 1 to about 12 carbon atoms, substituted or unsubstituted monocarboxcylic aryl radicals having from about 5 to abut 12 carbon atoms, substituted or unsubstituted monocarboxcylic arylalkyl radicals having from abut 6 to about 15 carbon atoms, alkoxyalkyl radicals having from about 2 to about 12 carbon atoms, and alkyloxy radicals having from 1 to about 12 carbon atoms. The mole ratio of the herbicidal pyridinedicarboxylate to the crystallizing inhibiting diester ranges from 5:95 to 95:5.

DETAILED DESCRIPTION OF THE INVENTION

The tendency of herbicidal pyridinedicarbothioates to crystallize and thus to partially lose their herbicidal activity when formulated in granular form is reduced by including in the granules a small but effective amount of certain diesters of alkylene dicarboxylic acids.

The present invention is more particularly concerned with reducing the tendency of the following herbicidal pyridinedicarbothioate from crystallizing when formulated as granules.

1. 3,5-pyridinedicarbothioic acid, 2-(difluoromethyl)-4-(2-methylpropyl)-6-(trifluoromethyl)-, S,S-dimethyl ester.

These just mentioned herbicides when used alone or as mixtures are particularly effective for use in controlling undesirable plants in transplanted rice crops. The application rates of these herbicides in controlling the unwanted plants range from about 0.01 to about 0.28 kilogram or more per hectare (kg/ha) of active.

The diesters of an alkylene dicarboxylic acid useful for preventing or suppressing the crystallization of the pyridinedicarbothioate herbicides may be represented by the following general formula

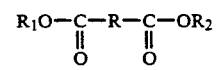

In the formula R is an alkylene radical having 1-12 carbon atoms. Examples of such radicals include methylene, propylene, butylene, pentylene, etc. $R_1$ and $R_2$ independently may be lower alkyl radicals having 1-12 carbon atoms, preferably 3-8 carbon atoms. Exemplary of the lower alkyl radicals are isopropyl, n-butyl, sec-butyl, isobutyl, tert-butyl, m-hexyl, 2-ethylhexyl, etc. $R_1$ and $R_2$ may be substituted and unsubstituted monocarbocylic aryl radicals having 5-12 carbon atoms. Exemplary of such aryl radicals are phenyl, 3-methylphenyl, 2,5-dimethylphenyl, 2-methyl-5-ethylphenyl, 2,5-diethylphenyl, etc. $R_1$ and $R_2$ may be substituted or unsubstituted monocyclic arylalkyl radicals having 6 to 15 carbon atoms. Exemplary of such arylalkyl radicals are benzyl, 1-phenylethyl, etc. $R_1$ and $R_2$ may be alkoxyalkyl radicals having 2-12 carbon atoms. Exemplary of such alkoxyalkyl are methoxymethyl, methoxyethyl, methoxypropyl, butoxymethyl, etc.

The mole ratio of crystallization suppressor to the active herbicidal may range from about 5:95 to 95:5, preferably 20:80 to 80:20.

The most preferred diester is diisobutyl adipate. Adipate esters may be prepared by known procedures. For example, adipic acid (MP 307° F., 153° C.) is readily esterified to form both the mono and diesters. Acid catalysts are normally used, but the reaction normally proceeds readily in the absence of a catalyst at elevated temperatures of 250°-300° C. (480°-572° F.) provided the water of reaction is removed. Tin compounds are also known to catalyze the esterification yielding a product of good purity. In addition to adipic acid, other dibasic acids can be esterified in like manner, including oxalic acid, malonic acid, succinic acid, glutaric acid, pimelic acid, etc. to form the esters of dicarboxylic acid.

Among the many adipate esters commercially available include diisobutyl adipate, dibutyl adipate, di-2-ethylhexyl adipate, diisononyl adipate, diisopropyl adipate, di-n-hexyl adipate, diisodecyl adipate, diethoxyethyl adipate, dibutoxyethyl adipate, dimethoxyethyl adipate, bis(butyldiglycol) adipate.

Herbicide-containing granules provides a convenience arrangement for delivering the herbicide to the locations where the plants are to be controlled. Granules are physically stable particulate compositions comprising herbicidally active ingredients adhering to or distributed through a basic matrix in an inert, finely-divided particulate extender. In order to aid leaching of the active ingredient or mixture of active ingredients from a particulate extender, surfactants can be present in the composition, including but not limited to surface active agents, such as polyoxyethylene-polyoxypropylene block polymer (Emalgen PP-150, Emalgen PP-230, Emalgen PP-250, Emalgen PP-290 of KAO Corp.), polyvinyl-pyrrolidone-vinyl acetate copolymer (Tokyo Kasei Kogyo Co. Ltd.) as well as other surface active agents, such as general anionic, cationic, nonionic and amphoteric surfactants. Natural clays, pyrophyllites, illite, and vermiculite are examples of operable classes of particulate mineral extenders. The preferred extenders are the porous, absorptive, preformed particles, such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.05 to about 30 parts by weight of active ingredient per 100 parts by weight of clay and 0 to about 10 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, sulfonylureas, dinitroanilines, carbamates, acetamides, acetanilides, uracils, acetic acid or phenol derivatives, thiolcarbamates, triazoles, benzoic acids, nitriles, diphenyl ethers and the like.

Fertilizers useful in combination with the active ingredients include, for example, ammonium nitrate, urea, potash and superphosphate. Other useful additaments include materials in which plant organisms take root and grow, such as compost, manure, humus, sand and the like.

Herbicidal formulations of the type described above are exemplified in several illustrative embodiments below.

The invention will now be further disclosed in the following illustrative example, wherein parts and percentages are given in a weight basis unless otherwise specified.

Storage Stability Test

In the examples the prepared granules were tested for the crystallization of the active pyridinedicarbothioate herbicide in the granules upon storage. In the storage stability test method employed, 10 grams of each sample is kept in a constant temperature and constant humidity incubator (Advantec, Model AE-215). The use of this equipment provides accurate control of both temperature and humidity for regulating temperature and humidity at 30° C. and 80%, respectively. After being in such controlled atmosphere for one week, each sample is checked under a microscope for the crystallization of the active herbicide. A flowering phenomenon of the active is indicative of the active having become at least partially crystallized.

EXAMPLE 1

This example illustrates the preparation of granules containing herbicidal pyridinecarbothioates.

In a mortar 72.1 grams of clay, 20.0 grams of bentonite, 5 grams of lignosulfonate and 1.0 gram of sodium alkylbenzene sulfonate were intimately mixed. Separately, a solution was made using 0.4 gram of 3,5-pyridinedicarbothioic acid, 2-(difluoromethyl)-4-(2-methylpropyl)-6-(trifluoromethyl)-, S,S-dimethyl ester, 0.5 gram of the mixed surfactant as shown below and 1.0 gram of the diisobutyl ester of adipic acid, sold by KAO Corp. under the name of Vinycizer-40®. The surfactant used was composed of:

15% POE styrylphenylether polymer
15% POE castor oil
15% POE fatty acid ester
35% alkylarylsulfonate
20% aromatic solvent The solution and the contents from the mortar were thoroughly mixed to form a solid powder mixture. To the powder 18 grams of water was added and the resulting mixture was mixed at room temperature for 15 minutes. The resulting mixture was a dough-like substance. The dough was then fed into a conventional laboratory extrusion device using screen holes of 0.8 mm diameter. The extruded material was in the form of granules (diameter 0.8 mm, length 5 mm) and was dried in an electrically heated oven over 2 hours at about 50° C. The resulting dry granules were sieved to 12/32 mesh using a standard shifter.

A second batch of granules was prepared in like manner with the adipic acid ester being omitted and a like amount of polyethylene glycol monomethylether was substituted therefore.

The granules containing the adipic acid ester (Comp. 1) and the granules not containing the adipic acid ester (Control 1) were stored for one week in a controlled atmosphere having a temperature of 30° C. and a relative humidity of 80. After being stored under these conditions, the granules were closely observed. In the control the herbicide particles appeared to be flowering which indicated that the active had crystallized out. In the granules containing the adipic acid ester, no flowering of the active was observed which indicated that the active had not crystallized.

EXAMPLE 2

In this example granules containing the same active herbicide as in Example 1 were prepared as described in Example 1 with (Comp. 2) and without (Control 2) the diisobutyl ester of adipic acid. In Table 1 the composition of Comp. 2 and Control 2, together with an observation as to the crystallizing of the active after storage of the granules are set forth. The amount of ingredients is given as weight percentages.

TABLE 1

| Ingredient | Control 2 | Comp. 2 |
|---|---|---|
| Active | 0.4 | 0.4 |
| Surfactant* | 1.0 | 1.0 |
| Polyethylene glycol methyl ether (MW = 220) | 1.0 | — |
| Adipic acid ester | — | 1.0 |
| Na tripolyphosphate | 2.0 | 2.0 |
| Na lignosulfonate | 5.0 | 5.0 |
| Surfactant** | 0.8 | 0.8 |
| Bentonite | 40 | 40 |
| Talc | 49.8 | 49.8 |
| Storage Stability | Flowering | No Flowering |

TABLE 1-continued

| Ingredient | Control 2 | Comp. 2 |
|---|---|---|
| Crystallization of active | yes | no |

*A polyoxyalkylene C₉ alkyl phenyl ether surfactant of Takemoto Oil and Fat Company.
**An aqueous solution of a surfactant of sodium polyacrylate (about 43%) of Sanyo Che. Ind. Ltd.

EXAMPLES 2-12

In these examples granules were prepared in accordance with Example 1 and they illustrate the use of various esters of adipic acid as crystallization suppressors. The various granular compositions made and tested and the results of crystallization suppression are given in Table 2.

TABLE 2

| | Example No. | | | | | | | | | |
|---|---|---|---|---|---|---|---|---|---|---|
| Ingredient | 3 | 4 | 5 | 6 | 7 | 8 | 9 | 10 | 11 | 12 |
| Active | 0.4 | 0.4 | 0.4 | 0.4 | 0.4 | 0.4 | 0.4 | 0.4 | 0.4 | 0.4 |
| Polyoxyalkylene C₉ alkylphenyl ether | 1.0 | 1.0 | 1.0 | 1.0 | 1.0 | 1.0 | 1.0 | 1.0 | 1.0 | 1.0 |
| Adipic acid diethyl ester | 1.0 | — | — | — | — | — | — | — | — | — |
| Adipic acid diisobutyl ester | — | 1.0 | — | — | — | — | — | — | — | — |
| Adipic acid diisodecyl ester | — | — | 1.0 | — | — | — | — | — | — | — |
| Adipic acid diallylester | — | — | — | 1.0 | — | — | — | — | — | — |
| Soybean oil | — | — | — | — | 1.0 | — | — | — | — | — |
| Tripopylene glycol | — | — | — | — | — | 1.0 | — | — | — | — |
| Polyethylene glycol monomethyl ether (MW = 200) | — | — | — | — | — | — | — | 1.0 | — | — |
| Na lignosulfonate | 5.0 | 5.0 | 5.0 | 5.0 | 5.0 | 5.0 | 5.0 | 5.0 | 5.0 | 5.0 |
| Na dodecylbenzene sulfonate | 1.0 | 1.0 | 1.0 | 1.0 | 1.0 | 1.0 | 1.0 | 1.0 | 1.0 | 1.0 |
| Bentonite | 20 | 20 | 20 | 20 | 20 | 20 | 20 | 20 | 20 | 20 |
| Talc | 71.6 | 71.6 | 71.6 | 71.6 | 71.6 | 71.6 | 71.6 | 71.6 | 72.6 | 72.6 |
| Crystallization of active | No | No | No | No | Yes | Yes | Yes | Yes | Yes | Yes |

EXAMPLES 13-16

In these examples granules were prepared in accordance with Example 1 and they illustrate the use of the diisobutyl ester of adipic acid as a crystallization suppressor in different granular compositions. For each composition a control was run where there was no adipic acid suppressor in the composition. The various granular compositions made and tested and the results of crystallization suppression are given in Table 3.

TABLE 3

| Ingredient | Control 13 | 13 | Control 14 | 14 | Control 15 | 15 | Control 16 | 16 |
|---|---|---|---|---|---|---|---|---|
| Active | 0.4 | 0.4 | 0.4 | 0.4 | 0.4 | 0.4 | 0.4 | 0.4 |
| Polyoxyalkylene C₉ alkylphenyl ether | 1.0 | 1.0 | 1.0 | 1.0 | 1.0 | 1.0 | 1.0 | 1.0 |
| Na Polyacrylate | 0.8 | 0.8 | 0.8 | 0.8 | 0.8 | 0.8 | 0.8 | 0.8 |
| Na lignosulfonate | 5.0 | 5.0 | 5.0 | 5.0 | 5.0 | 5.0 | 5.0 | 5.0 |
| Polyoxyethylene glycol-monomethyl ether (MW = 220) | 1.0 | — | 1.0 | — | 1.0 | — | 1.0 | — |
| Adipic acid diisobutyl ester | — | 1.0 | — | 1.0 | — | 1.0 | — | 1.0 |
| Na tripolyphosphate | 2.0 | 2.0 | 2.0 | 2.0 | 2.0 | 2.0 | 2.0 | 2.0 |
| Benotite | 89.8 | 89.8 | 40 | 40 | 40 | 40 | 40 | 40 |
| Kaolin clay | — | — | 49.8 | 49.8 | — | — | — | — |
| Calcium carbonate | — | — | — | — | 49.8 | 49.8 | — | — |
| Diatomaceous earth | — | — | — | — | — | — | 49.8 | 49.8 |
| Crystallization of active | Yes | No | Yes | No | Yes | No | Yes | No |

EXAMPLE 17

This example illustrates the preparation of sand granules containing the same active herbicide as in Example 1 with and without the adipic acid diisobutyl ester crystallization suppressor.

2.5 grams of the active herbicide, 0.5 gram of New Kalgen D-416P surfactant and 4.0 grams of adipic acid diisobutyl ester were added to a vessel. The resulting mixture was stirred with heating at 80° C. until a clear solution resulted. Then, 88.5 grams of sand granules (12/48 mesh) was added to a V Type Mixer. The solution containing the herbicide was dropped slowly onto the granules being stirred and mixed. After addition of the solution, mixing was continued for 5 minutes more. Thereafter, 4.5 grams of white carbon was added and the mixing was continued for an additional 10 minutes. The resulting herbicide coated sand granule was tested for storage stability. The results of this example are set forth in Table 4.

TABLE 4

| Ingredient | Control 17 | 17 |
|---|---|---|
| Active | 2.5 | 2.5 |
| Polyoxyalkylene C₉ alkylphenyl ether | 0.5 | 0.5 |
| Polyethyleneglycolmethyl ether (MW = 220) | 4.0 | — |
| Adipic acid diisobutyl ester | — | 4.0 |
| White carbon | 4.5 | 4.5 |
| Sand granules | 88.5 | 88.5 |
| Crystallization of active | Yes | No |

EXAMPLE 18

This example illustrates the preparation of extruded granules containing 3,5-pyridinedicarbothioic acid, 2-(difluoromethyl)-4-(2-methylpropyl)-6-(trifluoromethyl)-, S,S-dimethyl ester with and without a crystallization suppressor being employed in accordance with the present invention.

61.0 grams of clay, 30.0 grams of bentonite, 5.0 grams of sodium lignosulfate, and 1.0 gram of sodium dodecylbenzene sulfonate were combined and mixed in a mortar; and then, a solution which contained 2.5 grams of active, 0.5 gram New Kalgen ® D-416 and 5.0 grams of adipic acid diisobutylester was added slowly to the mixture in the mortar. The resulting mixture was a powder. Thereafter, the resulting mixture and 16 grams of water were kneaded together. The kneaded mixture had a dough-like consistency. The dough was then fed to a laboratory extruder and extruded through screen holes of 0.8 mm diameter. The extruder granules were dried in a fan electrical oven for 1.5 hours at 55° C. The dried granules were sieved by the use of a shifter to 12/32 mesh. The resulting granules were tested for storage stability. The results are set forth in Table 5.

TABLE 5

| Ingredient | Control 18 | 18 |
|---|---|---|
| Active | 2.5 | 2.5 |
| Polyoxyalkylene C9 alkylphenyl ether | 0.5 | 0.5 |
| Adipic acid diisobutyl ester | — | 5.0 |
| Na lignosulfonate | 5.0 | 5.0 |
| Na dodecylbenzene sulfonate | 1.0 | 1.0 |
| Bentonite | 30.0 | 30.0 |
| Pyrophilite clay | 61 | 56 |
| Crystallization of active | yes | no |

EXAMPLE 19

The herbicidal activities of various samples as prepared above were determined in a greenhouse on barnyardgrass at two different rates. When the herbicide was applied, the barnyardgrass had a leaf stage of 2.2. The percent control given in Table 6 below is an average of two tests.

TABLE 6

| Example No. | KGAI/HA* | 14 DAT** | 25 DAT | 35 DAT |
|---|---|---|---|---|
| Comp. 1 | 0.12 | 65 | 99 | 100 |
|  | 0.06 | 42 | 72 | 80 |
| Control 1 | 0.12 | 52 | 90 | 89 |
|  | 0.06 | 27 | 55 | 47 |
| Comp. 2 | 0.12 | 60 | 93 | 100 |
|  | 0.06 | 55 | 92 | 85 |
| Control 2 | 0.12 | 55 | 95 | 96 |
|  | 0.06 | 37 | 60 | 47 |

*KGAI/HA = kilogram of active ingredient per hectare
**DAT = number of days after treatment As can be seen from the above, the pyridinedicarbothioate herbicide manifesting crystallization has reduced herbicidal activity as compare to the same herbicide whose crystallization is suppressed by an alkyl ester of an alkylene dicarboxylic acid.

While the illustration embodiments of the invention have been described with particularity, it will be understood that various other modifications will be apparent or can be readily made by those skilled in the art without departing from the spirit and scope of the invention. Accordingly, it is not intended that the scope of the claims appended hereto be limited to the examples and description as set forth hereinabove but rather that the claims be construed as encompassing all the features of patentable novelty which reside in the present invention, including all features which would be treated as equivalents thereof by those skilled in the art.

What is claimed:

1. A herbicidal composition comprising a mixture of a pyridinedicarbothioate herbicide and a pyridinedicarbothioate crystallization suppressing amount of an alkylene dicarboxylic acid ester.

2. A granule made from the composition of claim 1.

3. The herbicidal composition of claim 1 wherein the alkylene dicarboxylic acid ester is represented by the formula

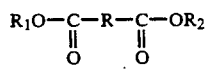

wherein R is an alkylene radical having from 1 to about 12 carbon atoms and $R_1$ and $R_2$ are selected from the group consisting of alkyl radicals having 1 to 12 carbon atoms, substituted or unsubstituted monocarbocylic aryl radicals having from 5 to 12 carbon atoms, substituted or unsubstituted monocarbocylic arylalkyl radicals having from 6 to 15 carbon atoms, alkoxyalkyl radicals having from 2 to 12 carbon atoms, and alkyloxy radicals having from 1 to 12 carbon atoms.

4. The composition of claim 3 wherein the alkylene dicarboxylic acid ester is dibutyl adipate, diisobutyl adipate, di-2-ethylhexyl adipate, diisononyl adipate, diisopropyl adipate, di-n-hexyl adipate, diisodecyl adipate, diethoxyethyl adipate, dibutoxyethyl adipate, dimethoxymethyl adipate or bis(butyldiglycol) adipate.

5. The composition of claim 1 wherein the active herbicide is 3,5-pyridinedicarbothioic acid, 2-(difluoromethyl)-4-(2-methylpropyl)-6-(trifluoromethyl)-, S,S-dimethyl ester.

6. The composition of claim 5 wherein the alkylene dicarboxylic acid ester is dibutyl adipate, diisobutyl adipate, di-2-ethylhexyl adipate, diisononyl adipate, diisopropyl adipate, di-n-hexyl adipate, diisodecyl adipate, diethoxyethyl adipate, dibutoxyethyl adipate, dimethoxylmethyl adipate or bis(butyldiglycol) adipate.

* * * * *